(12) United States Patent
Fransson et al.

(10) Patent No.: US 11,191,903 B2
(45) Date of Patent: Dec. 7, 2021

(54) SYRINGE PLUNGER ROD

(71) Applicant: SWEDISH ORPHAN BIOVITRUM AB (PUBL), Stockholm (SE)

(72) Inventors: Jonas Fransson, Uppsala (SE); Hans Himbert, Stockholm (SE); Pelle Reinius, Enskede (SE)

(73) Assignee: SWEDISH ORPHAN BIOVITRUM AB (PUBL), Stockholm (SE)

( * ) Notice: Subject to any disclaimer, the term of this patent is extended or adjusted under 35 U.S.C. 154(b) by 0 days.

(21) Appl. No.: 15/303,558

(22) PCT Filed: Apr. 14, 2015

(86) PCT No.: PCT/EP2015/058063
§ 371 (c)(1),
(2) Date: Oct. 12, 2016

(87) PCT Pub. No.: WO2015/158707
PCT Pub. Date: Oct. 22, 2015

(65) Prior Publication Data
US 2017/0028135 A1 Feb. 2, 2017

(30) Foreign Application Priority Data
Apr. 14, 2014 (EP) ..................... 14164619

(51) Int. Cl.
*A61M 5/31* (2006.01)
*A61M 5/315* (2006.01)

(52) U.S. Cl.
CPC .......... *A61M 5/3148* (2013.01); *A61M 5/315* (2013.01); *A61M 5/3129* (2013.01);
(Continued)

(58) Field of Classification Search
CPC .... A61M 5/31511; A61M 2005/31508; A61M 5/31501; A61M 5/315; A61M 2005/3139;
(Continued)

(56) References Cited

U.S. PATENT DOCUMENTS 4,325,369 A * 4/1982 Nilson .................... A61J 1/062
604/214
5,024,662 A 6/1991 Menes et al.
(Continued)

FOREIGN PATENT DOCUMENTS

CN 201410189 Y 2/2010
CN 201469819 U 5/2010
(Continued)

OTHER PUBLICATIONS

International Search Report and Written Opinion were dated May 19, 2015 for International Application No. PCT/EP2015/058063, which was filed on Apr. 14, 2015 and published as WO/2015/158707 dated Oct. 22, 2015 (Inventor—Jonas Fransson; Applicant—Swedish Orphan BioVitrum AB) (11 pages).

(Continued)

*Primary Examiner* — Emily L Schmidt
*Assistant Examiner* — Leah J Swanson
(74) *Attorney, Agent, or Firm* — Ballard Spahr LLP

(57) ABSTRACT

The present invention relates to a syringe having a barrel, a plunger arranged to travel within said barrel and a plunger rod for driving the plunger in a bidirectional manner. The plunger rod is provided with a head at a distal end thereof and a plurality of protruding finger grip enhancing means axially spaced along a length of the plunger rod.

18 Claims, 4 Drawing Sheets

(52) U.S. Cl.
CPC ...... *A61M 5/3137* (2013.01); *A61M 5/31595* (2013.01); *A61M 2005/3139* (2013.01); *A61M 2207/00* (2013.01)

(58) Field of Classification Search
CPC .............. A61M 5/3148; A61M 5/3137; A61M 5/31595; A61M 5/31593; A61M 5/31505; A61M 2005/31506; A61M 5/31525; A61M 5/3153; A61M 5/31565; A61M 2005/3144; A61M 2005/31516; A61M 2005/31523; A61M 2005/5033
USPC ......... 128/919; 604/110, 187, 207, 210, 218
See application file for complete search history.

(56) References Cited

U.S. PATENT DOCUMENTS

| | | | | |
|---|---|---|---|---|
| 5,059,181 | A * | 10/1991 | Agran | A61M 5/5013 128/919 |
| 5,215,536 | A * | 6/1993 | Lampropoulos | A61M 5/315 604/187 |
| 5,395,339 | A * | 3/1995 | Talonn | A61M 5/31511 604/110 |
| 5,433,007 | A * | 7/1995 | Clark | B25C 3/006 30/360 |
| 5,478,311 | A * | 12/1995 | Klearman | A61J 7/0007 241/DIG. 27 |
| 5,582,595 | A | 12/1996 | Haber et al. | |
| 6,565,529 | B1 * | 5/2003 | Kimber | A61M 5/3135 604/110 |
| 8,267,902 | B2 | 9/2012 | Martinsson | |
| 8,394,068 | B2 * | 3/2013 | Kosinski | A61M 5/31511 604/219 |
| 9,616,175 | B2 * | 4/2017 | Bom | A61M 5/24 |
| 2004/0006314 | A1 * | 1/2004 | Campbell, Jr. | A61M 5/3234 604/218 |
| 2004/0254539 | A1 | 12/2004 | Wolbring et al. | |
| 2008/0188799 | A1 * | 8/2008 | Mueller-Beckhaus | A61J 1/2096 604/88 |
| 2010/0076370 | A1 * | 3/2010 | Howlett | A61M 5/1424 604/65 |
| 2010/0076378 | A1 | 3/2010 | Runfola | |
| 2012/0029471 | A1 | 2/2012 | Lee et al. | |
| 2014/0171862 | A1 | 6/2014 | Weidner | |
| 2015/0057608 | A1 * | 2/2015 | Hitscherich, Jr. | A61M 5/3137 604/91 |
| 2015/0105754 | A1 * | 4/2015 | Roche | A61M 1/007 604/542 |

FOREIGN PATENT DOCUMENTS

| | | | | |
|---|---|---|---|---|
| CN | 102458510 A | 5/2012 | | |
| CN | 102481418 A | 5/2012 | | |
| DE | 1053143 | 3/1959 | | |
| FR | WO 2013132192 A1 * | 9/2013 | ............ | A61M 1/007 |
| JP | S5734860 A | 2/1982 | | |
| JP | H10277153 A | 10/1998 | | |
| JP | 2003/521974 A | 7/2003 | | |
| RU | 2454250 C2 | 6/2012 | | |
| RU | 2483759 C2 | 6/2013 | | |
| WO | WO 1989/009071 | 10/1989 | | |
| WO | WO 1989/012476 | 12/1989 | | |
| WO | WO 1994/013339 | 6/1994 | | |
| WO | WO-95/16427 A1 | 6/1995 | | |
| WO | WO-01/05456 A1 | 1/2001 | | |
| WO | WO 2008/057976 | 5/2008 | | |
| WO | WO-2008/154615 A1 | 12/2008 | | |
| WO | WO 2012/020957 | 2/2012 | | |
| WO | WO-2012020957 A2 * | 2/2012 | ......... | A61B 5/15003 |
| WO | WO-2013/010631 | 1/2013 | | |
| WO | WO-2013/132192 A1 | 9/2013 | | |

OTHER PUBLICATIONS

International Preliminary Report on Patentability was dated Oct. 18, 2016 by the International Searching Authority for International Application No. PCT/EP2015/058063, filed on Apr. 14, 2015 and published as WO/2015/158707 dated Oct. 22, 2015 (Applicant—Swedish Orphan Biovitrum AB) (7 Pages).

\* cited by examiner

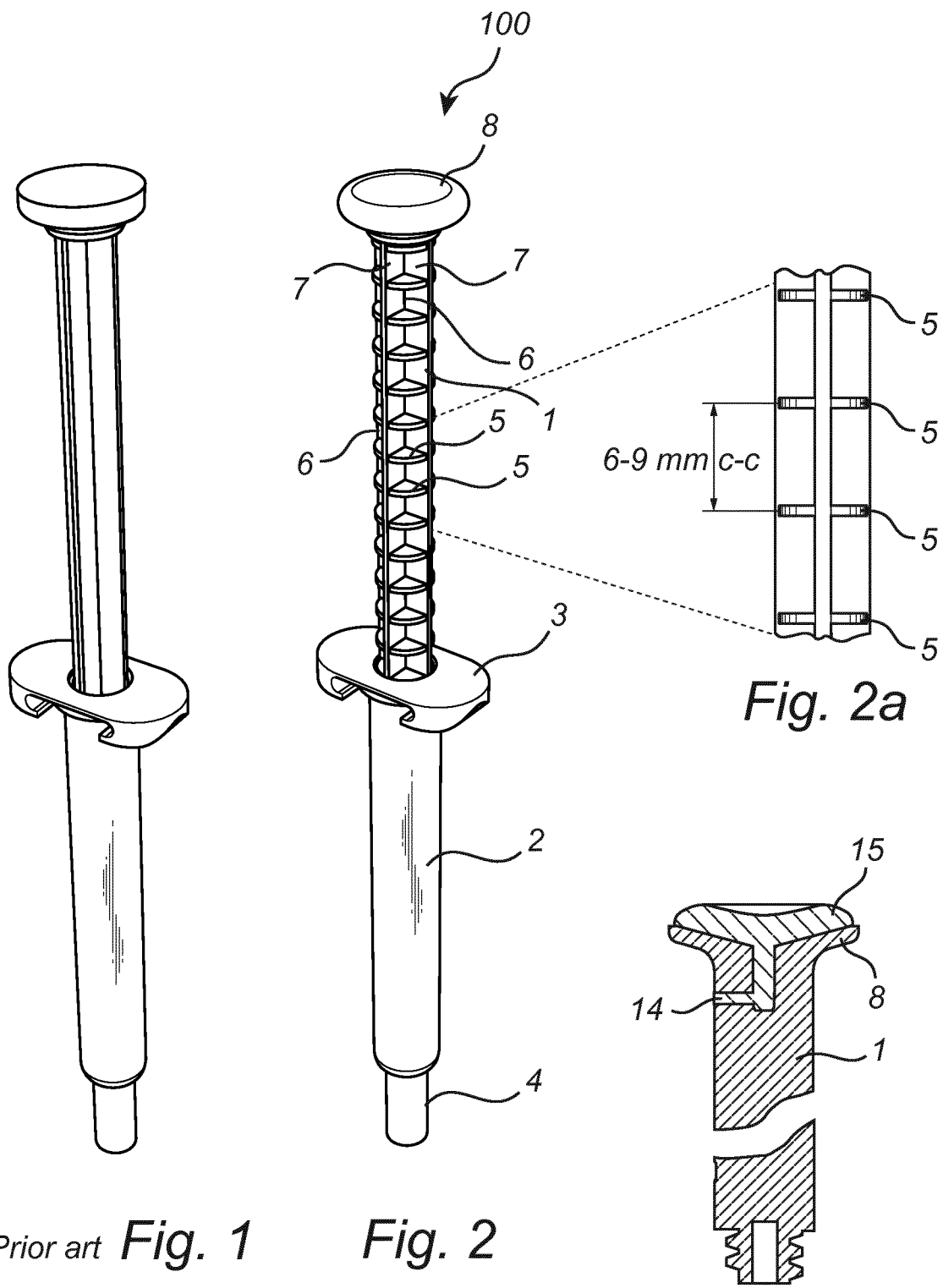

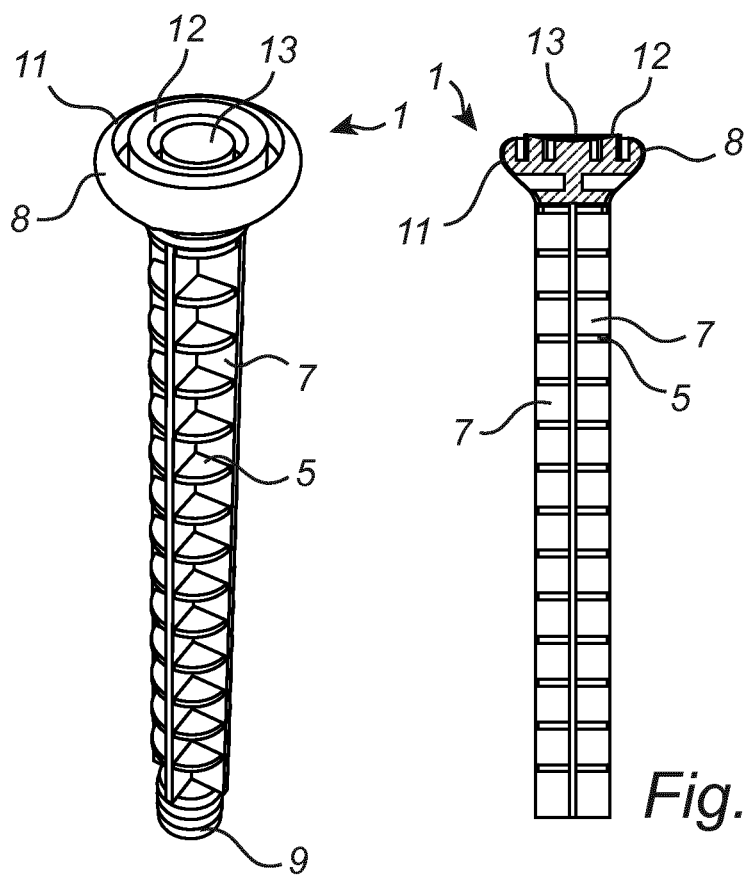
Fig. 4a
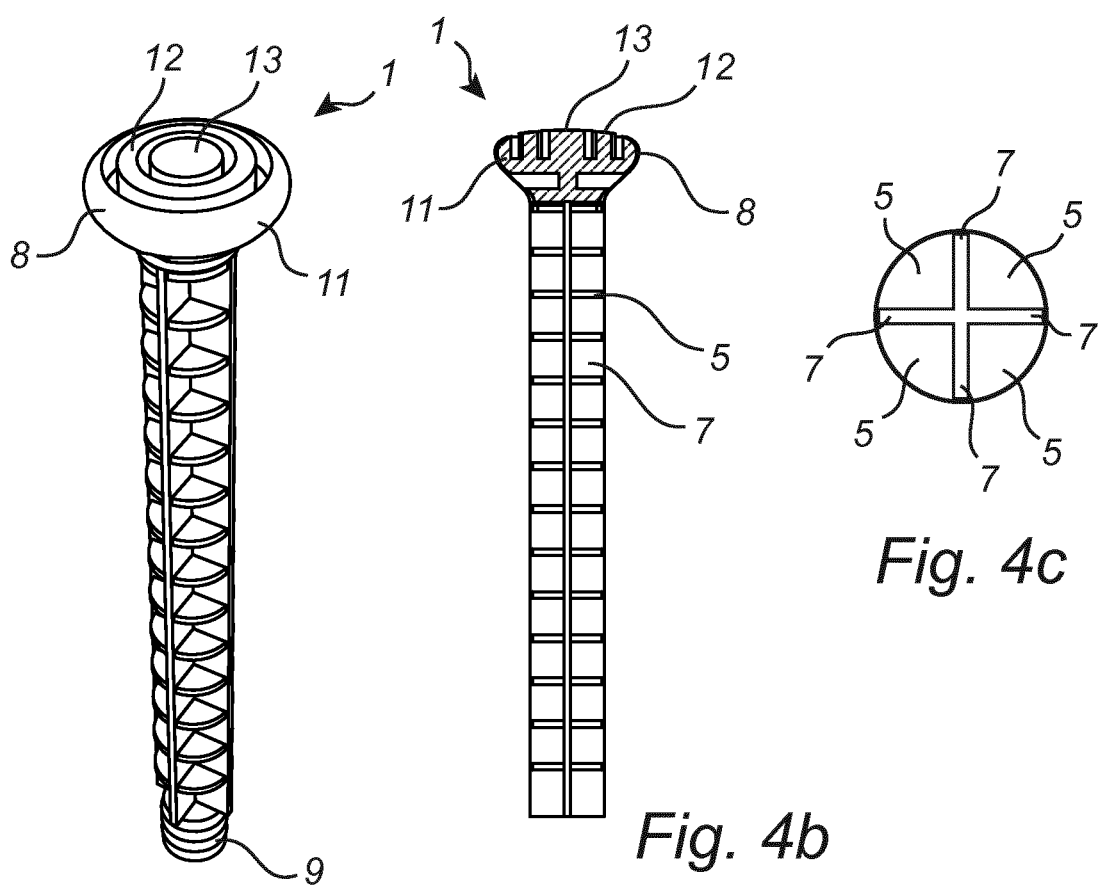
Fig. 4c
Fig. 4b

SYRINGE PLUNGER ROD

CROSS-REFERENCE TO RELATED APPLICATIONS

This application is a U.S. National Phase Application of International Application No. PCT/EP2015/058063, filed Apr. 14, 2015, which claims priority to European Patent Application No. 14164619.0, filed Apr. 14, 2014, each of which are hereby incorporated by reference in their entirety.

FIELD OF THE INVENTION

The present invention relates to a medical syringe, especially a medical syringe adapted to both draw and deliver a liquid.

BACKGROUND OF THE INVENTION

Medical syringes are normally used to deliver materials such as medicaments during a therapeutic injection to a patient. Syringes may also be arranged to take in materials, for example withdrawing blood from a patient. In certain fields of application it is also necessary to provide a medical syringe that can handle both withdrawal and injection. Treatment of haemophilia is one such application. Here, a patient is required to first fill the barrel of a medical syringe with a prescribed amount of a drug. This is done by inserting the needle of the syringe into a receptacle containing the drug and thereafter filling the barrel by pulling the plunger rod, and thus also the plunger, backwards until the required amount has been sucked into the barrel. The patient then inserts the needle of the syringe into a blood vessel (a vein) at a suitable place on his body such that the drug can be injected. However, it is of utmost importance that the needle is actually inserted into a vein and therefore the patient aspirates to make sure that this is the case, i.e. the plunger rod is retracted when the needle is inserted into the body. If blood appears in the barrel of the syringe, the patient can normally safely assume that the needle is indeed correctly inserted into a vein and can proceed with the injection of the drug. A syringe arranged to simplify aspiration is disclosed in prior art document U.S. Pat. No. 5,582,595. That prior art comprises a medical syringe having two pairs of finger grips, a first pair provided at the distal end of the barrel for use during injection and a second pair provided at the head of the plunger rod for use during aspiration. That prior art further comprises a thumb base arranged at distal ends of a pair of longitudinally extending plunger guides. During aspiration a user of that prior art places the thumb on the thumb base and the forefinger and the middle finger on the second pair of finger grips and axially pulls the plunger rod backwards such that aspiration is performed. For injection, the thumb has to be inserted between the plunger guides and placed on the plunger head and the forefinger and middle finger are placed on the first pair of finger grips and the plunger rod is pushed such that a medicament is expelled from the barrel. However, despite the improvements described therein, that prior art still has drawbacks when it comes to user friendliness and ergonomics, both during aspiration and injection with the syringe. For example, since the thumb has to be inserted between the plunger guides, the number of grip positions available to a user is greatly reduced. Further, that prior art also has a complicated structure making it expensive to manufacture and it requires the user to perform additional assembly in that it is necessary to assemble the thumb base to the plunger guides after assembly of the plunger rod to the plunger. Another known solution is described in WO-89/09071. That prior art document also describes a rather complicated structure provided with a number of finger flanges arranged to provide a number of possible positions during injection. However, nothing is done in that prior art to alleviate aspiration.

SUMMARY OF THE INVENTION

It is therefore an object of the present invention to provide a medical syringe with improved user friendliness and ergonomics. This object and other objects are solved by a syringe as defined in claim 1. This object and other objects are also solved by a kit of parts as defined in claim 16 and by a plunger rod as defined in claim 18 and the method for manufacturing a plunger rod as defined in claim 19. Preferred embodiments of the present invention are defined in the dependent claims.

Thus, in accordance with an aspect of the present invention, there is provided a syringe having a barrel, a plunger arranged to travel within the barrel and a plunger rod for driving the plunger in a bidirectional manner. The plunger rod is provided with a head at a distal end, i.e. the end pointing away from the plunger and the needle. The plunger rod further comprises a plurality of protruding finger grip enhancing means axially spaced along a length of the plunger rod and these finger grip enhancing means are provided with a mutual center distance between 3 and 20 mm, preferably between 5 and 10 mm and most preferably between 6 and 9 mm. These finger grip enhancing means provide a major advantage over the prior art solutions in that it allows a patient to securely manipulate the plunger rod itself when performing different actions. For example, when a patient assembles a new, unused syringe the plunger rod needs to be fixed to the plunger. Typically the plunger rod is provided with a threaded portion which can be screwed into the plunger and this threaded connection between the plunger rod and the plunger provides a connection between the two parts that allows the plunger rod to drive the plunger in both directions. The finger grip enhancing means of the plunger rod according to the present invention facilitates this assembling in comparison with the plunger rods of prior art solutions having a more or less smooth outer surface. Another situation where the plunger rod of the present invention provides for enhanced ergonomics and user friendliness is where a patient is required to draw up a drug into the barrel of the syringe or during aspiration of an inserted syringe. In these cases, it is not always possible to use both hands, one firmly holding the syringe and the other pulling the plunger rod backwards by grasping the head of the plunger rod, but instead only one hand is available. U.S. Pat. No. 5,582,595 discloses a solution to this problem where two pairs of finger grips and a thumb base is provided such that aspiration can be performed with one hand only. This solution has a major disadvantage in that a patient with small hands, e.g. a child, is not always able to reach all the way between the head of the plunger and the second pair of finger grips, especially in situations where the plunger rod is still in a most proximal position, e.g. at an initial stage of aspiration when the barrel is still completely empty. This would force the patient to reach out for the thumb base in an uncomfortable manner. Apart from being inconvenient, this has another drawback in that such reaching and stretching could cause unintentional moving of the inserted syringe in the body of the patient, thus possibly causing micro bleeds, or worse, which of course is very inconvenient for patients with haemophilia or similar. The same disadvantages of that prior art apply analogously during injection of the drug, or at least during an initial part of the injection until the patient is able to comfortably reach the upper side of the plunger rod head and most certainly for persons with small hands. The plunger rod of the present invention evade these problems by providing good gripping properties along a length of the plunger rod such that a patient can place one or more fingers on the outer surface of the plunger rod and perform the desired action, e.g. aspiration, injection or assembly of syringe, without having to use the head of the plunger rod. During aspiration and injection, a patient holding the barrel of the syringe with the fingers within the palm can place the thumb anywhere on the outer surface of the plunger rod along the length thereof and push or pull the plunger rod as desired using one hand only. The provision of finger grip enhancing means arranged with a mutual center distance between 3 and 20 mm has been shown to ensure good gripping properties. Too few, i.e. too great distance between adjacent finger grip enhancing means, means that a user would possibly have access to no finger grip enhancing means at all at a position where she or he would desire to place e.g. the thumb. On the other hand, by providing too many finger grip enhancing means the result would be a more or less smooth surface which will possibly not provide the required effect of improved gripping properties and add unnecessarily to consumption of materials. It has been found that a mutual center distance between the finger grip enhancing means of between 3 and 20 mm fulfils these requirements. It is also possible to arrange finger grip enhancing means with different mutual center distance over different parts of the plunger rod. For example, adjacent gaps of a cross-shaped plunger rod can be provided with finger grip enhancing means having differing mutual center distance. This will satisfy divergent requirements from users.

In accordance with an embodiment of the syringe according to the invention, the finger grip enhancing means comprises a plurality of protruding ribs which are axially spaced along the length of the plunger rod and which extend generally perpendicularly to the longitudinal axis of the plunger rod. The provision of such ribs ensures good gripping properties, especially for pushing and pulling the plunger rod in an axial direction.

In accordance with an embodiment of the syringe according to the invention, the finger grip enhancing means comprises a plurality of disc-shaped elements which are axially spaced along the length of the plunger rod. The disc-shaped elements lie in a plane which is generally perpendicular to the longitudinal axis of the plunger rod. Similar to the ribs mentioned above, the provision of such disc-shaped elements ensures good gripping properties, especially for pushing and pulling the plunger rod in an axial direction.

In accordance with an embodiment of the syringe according to the invention, the plunger rod has a cross-shaped cross-section and the finger grip enhancing means are arranged in a gap that is defined by two adjacent legs of the cross-shaped plunger rod. The finger grip enhancing means may comprise a plurality of circle sector shaped grip elements. The circle sector shaped grip elements are axially spaced along the length of the plunger rod and lie in planes generally perpendicular to the longitudinal axis of the plunger rod. The use of plunger rods having cross-shaped cross-section is known since long and combines efficient use of materials with acceptable rigidity and ease of manufacture. However, the smooth surface of that construction provides no, or at least very little, friction for a patient who wants to push or pull the plunger rod in an axial direction, especially when using only one finger, such as the thumb.

The provision of a plurality of circle sector shaped grip elements between the legs of the plunger rod ensures that a surface is furnished on the plunger rod that provide improved gripping properties such that a user can apply a force on the plunger rod itself without having to reach the head of the plunger rod. Of course other shapes than circle sectors can be arranged that provide the same advantages. For example could an elliptical sector be imagined or similar.

In accordance with an embodiment of the syringe according to the invention, the arcs of the circle sectors extend between the tips of the two adjacent legs of the plunger rod. The fact that the grip elements are shaped as circle sectors and the respective arc of those circle sectors extend between the tips of the legs of the plunger rod means that any point along the arc between the tips of the legs will lie outside an imaginary straight line between the tips of the legs, in a way protruding from the plunger rod, thus providing good gripping properties to a user. Many other shapes of the finger grip enhancing means are of course imaginable, such as elliptical. As long as at least a part of the arc, that is the outer periphery of the finger grip enhancing means, lies outside an imaginary straight line between the tips of the legs the advantages according to the present invention will apply.

In accordance with an embodiment of the syringe according to the invention, the radii of the circle sectors are greater than the length of the two adjacent legs of the plunger rod. In comparison to the previous embodiment, this creates even better gripping properties to a user.

In accordance with an embodiment of the syringe according to the invention, circle sector shaped grip elements are arranged in at least two gaps of the plunger rod. For example, two opposing gaps can be provided with grip elements thus ensuring that a user always has a surface that provide improved gripping properties at hand. Of course, it is also conceivable to provide all four gaps of the plunger rod with grip elements to maximise user friendliness and ergonomics. Again, other shapes than circle sectors are imaginable.

In accordance with an embodiment of the syringe according to the invention, a finger grip enhancing means has a thickness of approximately 0.5-3 mm, preferably approximately 1 mm. Similar to the issue of the mutual distance between the finger grip enhancing means, it is important that the thickness, that is the height of the finger grip enhancing means in a direction parallel to the longitudinal direction of the plunger rod, is chosen correctly. A to small thickness will be perceived as being too sharp-edged and even flimsy whereas a too thick means will lose its friction enhancing properties and add unnecessarily to consumption of materials.

In accordance with an embodiment of the syringe according to the invention, the finger grip enhancing means are provided along substantially the whole length of the part of the plunger rod extending from an underside of the head to a connecting part of the plunger rod. This provides the user with the possibility to obtain a secure grip against the plunger rod independent of hand and finger size and in all positions of the plunger rod relative to the barrel.

In accordance with an embodiment of the syringe according to the invention, the plunger rod has a length such that when it has been fully depressed relative to the barrel, the plunger rod extends at least 8 mm beyond a distal end of barrel, measured from an underside of the head of the plunger rod. This means that it is much easier for a user to access the plunger rod and pull it upwardly, for example during filling of the barrel. Normally, plunger rods of syringes only extend about 4-5 mm beyond a distal end of the barrel making it hard to access the plunger rod when in a fully depressed state.

In accordance with an embodiment of the syringe according to the invention, the head of the plunger rod is provided with finger grip enhancing means. User friendliness is further enhanced by avoiding such means reducing the risk of slippage.

In accordance with an embodiment of the syringe according to the invention, the finger grip enhancing means of the head of the plunger rod comprises a rib extending in a direction generally parallel to the longitudinal axis of the plunger rod. An axially protruding rib will drastically improve friction and minimize the risk of slipping with the finger while applying pressure on the head of the plunger rod.

In accordance with an embodiment of the syringe according to the invention, the rib has an annular shape. The annular shape minimizes risk of slippage in all directions.

In accordance with an embodiment of the syringe according to the invention, the finger grip enhancing means of the head of the plunger rod comprises a thermoplastic elastomer (TPE). A layer of TPE can be applied to the upper, distal, surface of the plunger rod head providing anti-slip properties and a pleasant soft to the touch feeling for a user.

In accordance with an embodiment of the syringe according to the invention, the head of the plunger rod has a concave shape. The concave shape further enhances anti-slip properties of the head of the plunger rod by allowing a finger tip to rest in the thus created recess.

In accordance with an embodiment of the syringe according to the invention, the head of the plunger rod has a convex shape. The convex shape of the head of the plunger rod will also enhance anti-slip properties since the convex shape itself will create a kind of protrusion that will be pressed into the finger tip of the user when depressing the plunger rod.

In accordance with an embodiment of the syringe according to the invention, the barrel is of a two-chamber type having two chambers 2a and 2b, and a separator 30a to provide for separation of the chamber 2a and chamber 2b.

In accordance with another embodiment of the invention, a kit of parts is provided. This kit of parts comprises infusion equipment and a medicament to be injected. The infusion equipment in turn comprises a syringe according to the present invention. It should be noted in this respect that the medicament can be provided in a separate receptacle or already in a barrel of a syringe. For example, when treating haemophilia, the medicament is normally provided in the form of a powder which is mixed with water (or other suitable solvent) prior to treatment. This powder can be provided in a separate receptacle and mixed with e.g. water before it is drawn up into the syringe prior to infusion. Another possibility is to provide a prefilled two-chamber injector containing both powder and solvent such that preparation can be performed without any intermediate steps comprising transfer between separate receptacles. This embodiment of the invention is considered to cover both these aspects. The syringe of the present invention is considered to be particularly suitable for self administration by the patient of medicaments for intravenous injection such as haemophilia, hereditary angioedema, von Willebrand disease, analgesics, immunoglobulins, interferons, antibiotics, breast or prostate cancer etc. This due to the provision of the grip enhancing means on the plunger rod as described elsewhere in this application.

In accordance with another embodiment of the invention, a plunger rod for driving a plunger in a bidirectional manner within a barrel of a syringe is provided. The plunger rod comprises a head at a distal end thereof and further comprises a plurality of protruding finger grip enhancing means axially spaced along a length thereof. The finger grip enhancing means are provided with a mutual center distance between 3 and 20 mm, preferably between 5 and 10 mm and most preferably between 6 and 9 mm.

In accordance with another embodiment of the invention, a method for manufacturing a plunger rod by injection moulding is provided. The plunger rod comprises a head at a distal end thereof and a plurality of protruding finger grip enhancing means axially spaced along a length of the plunger rod. The finger grip enhancing means are provided with a mutual center distance between 3 and 20 mm, preferably between 5 and 10 mm and most preferably between 6 and 9 mm.

In accordance with an embodiment of the method according to the present invention, a thermoplastic elastomer is provided by injection moulding at a distal end of the head of the plunger rod.

In accordance with an embodiment of the method according to the present invention, the thermoplastic elastomer (TPE) is injected through a channel extending through plunger rod. This has the advantage that the distal surface of the TPE will have a smooth appearance without any protruding knobs resulting from the injection moulding and it also has substantial advantages concerning manufacturing complexity.

BRIEF DESCRIPTION OF THE DRAWINGS

The invention will now be described in more detail and with reference to the appended drawings in which:

FIG. 1 is a schematic perspective view of a syringe according to the prior art.

FIG. 2 is a schematic perspective view of an embodiment of the syringe according to the invention.

FIG. 2a is detail of the embodiment as shown in FIG. 2.

FIG. 2b. is a cross-section of an embodiment of the head of the plunger rod according to the invention

FIGS. 4a and 4b. are schematic perspective and side views of an embodiment of the syringe according to the invention.

FIG. 4c is a cross-section of an embodiment of the plunger rod according to the invention.

DESCRIPTION OF PREFERRED EMBODIMENTS

Figure 3A:
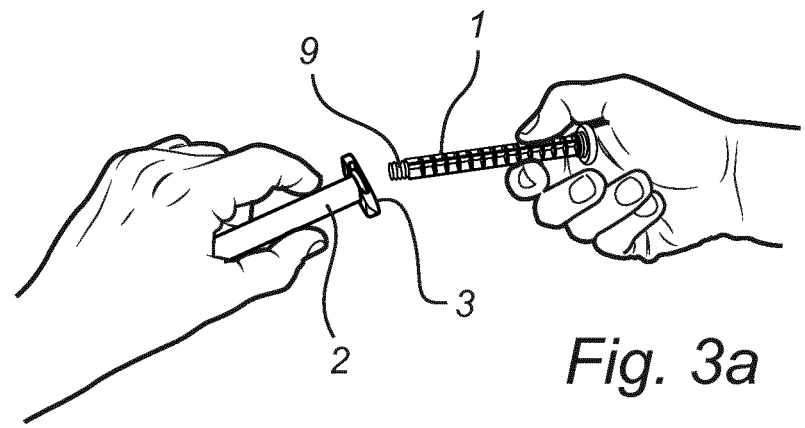
FIGS. 3a-3c are schematic perspective views of different modes of an embodiment of the syringe according to the invention.

In FIG. 1, a syringe as known from the prior art is shown. That syringe comprises a plunger rod having a generally cross-shaped cross-section along a major part of its axial length. A substantial drawback of that prior art is that aspiration and injection can only be done by manipulating the head of the plunger rod. As described above, this implies a number of disadvantages, for example when a user can use one hand only. Also, the plunger rod of that prior art is impractical during assembly of the syringe since the smooth surface thereof renders it difficult for a user to apply a force towards the plunger while screwing on the plunger rod to the plunger.

The present invention now presents the possibility that a user may apply a thumb against the outer surface of the plunger rod for moving it back and forth. If this should be done with a syringe according to FIG. 1, the user has either to insert the thumb within the gap created between two adjacent legs of the cross-shaped plunger rod having substantially smooth outer surfaces or position the thumb on the outer tip of one of the legs of the cross-shaped plunger rod. Neither of these alternatives represents a good alternative for anybody who wishes to manipulate the plunger rod during treatment, be it during aspiration, injection or filling of the barrel.

In a first embodiment of a syringe 100 according to the invention, as shown in FIG. 2, a syringe 100 comprises a plunger rod 1, a barrel 2, finger grips 3 and a plunger arranged within the barrel 2 (not shown in the figures). For the sake of completeness, it is stated that the barrel 2 is arranged to be equipped with a needle, not shown in the figures, by means of any suitable means, such as a Luer-Lok or Luer-Slip (registered Trademarks), at a proximal end 4 thereof. Concerning the terms "distal" and "proximal", throughout this document they refer to points which are further away and closer to the injection site respectively. The barrel 2 and finger grips 3 will not be closer discussed herein but are known from prior art and by the person skilled in the art.

Figure 3B:

As can be seen in FIGS. 2-4, the plunger rod 1 is provided with horizontally protruding grip enhancing means 5. In the figures they are provided as circle sector shaped elements 5 arranged within the gap 6 which is created between the separate legs 7 of the cross-shaped plunger rod 1. However, as disclosed elsewhere in this document, the grip enhancing means 5 do not necessarily have to be in the shape of circle sectors. In one embodiment, seen best in FIG. 4c, the arc of each circle sector 5 extends between the outermost tips of two adjacent legs 7, implying that the radii of the circle sector shaped elements 5 are the same as the length of the legs 7. This has the effect that any point along the arc between the tips of the legs 7 will lie outside an imaginary straight line between the tips of the legs 7 in a way protruding from the plunger rod 1 such that good friction properties are provided when a user grips the plunger rod 1. It is also conceivable that the radii of the circle sector shaped elements 5 are greater than the length of the legs 7 thereby creating even better qualities when it comes to axial displacement of the plunger rod 1. It is even possible within the scope of the present invention to arrange circle sector shaped elements 5 that have a radius that is somewhat smaller than the length of the legs 7. This since the arc of the circle sector shaped elements 5 will still protrude at least in part beyond an imaginary straight line between the tips of the legs 7. This would have an advantage over at least the embodiment where the radii of the circle sector shaped elements 5 are greater than the length of the legs 7 in that the tips of the legs 7 will protrude somewhat from the ends of each arc thereby providing an additional amount of friction during e.g. rotational movement, such as when a plunger rod 1 is to be assembled with the plunger in the barrel 2, see also FIG. 3b. This is of particular importance for users with impaired abilities to move, disabled persons or persons with reduced strength in arms and hands. Further, the plunger rod 1 comprises a head 8 which of course can also be used to manipulate the plunger rod 1. Head 8 is in FIG. 2 provided with a substantially smooth concave recess towards a user which improves anti-slip properties during use. As indicated with respect to FIGS. 4a and 4b, a convex shape is also possible. The head 8 may be provided with an outermost layer of thermoplastic elastomer (TPE) providing anti-slip properties and a pleasant soft to the touch feeling for a user.

FIG. 2a, which is an enlargement of a part of the plunger rod 1 as shown in FIG. 2 discloses the distance between two adjacent finger grip enhancement means 5 according to an embodiment of the present invention. During user research done on haemophilia patients, it was shown that the provision of finger grip enhancement means 5 provides for an improved ease of use, especially for users having a limited range of motion (e.g. children) and/or limited physical capacities (such as elderly). The test included 10 haemophilia patients, of which 3 were children aged 10-14 years; 2 were young adults in their twenties; and 5 were middle-aged to elderly (50-67 years old). The patients were asked to provide their opinion on syringes having three different plunger rods; an ordinary syringe having a cross-shaped cross-section with substantially smooth outer surfaces; a first syringe according to the present invention wherein the finger grip enhancing means (5) are provided with a mutual center distance of 9 mm; and a second syringe according to the present invention wherein the finger grip enhancing means (5) are provided with a mutual center distance of 6.1 mm. The outcome of the user research was that none of the patients preferred the traditional plunger rod over the two plunger rods of the present invention. The traditional plunger rod was perceived as slippery, unstable and as having sharp edges. The plunger rods according to the present invention on the other hand were perceived as more stable and providing superior grippability when aspirating as well as when twisting the syringe into place. Thus, it seems that providing finger grip enhancing means (5) with a mutual distance of between 6 and 9 mm is suitable to obtain good grippability for injection, aspirating and twisting required for mounting the syringe. The fact that a part of the plunger rod remained above the distal end of the barrel and finger grip also when fully depressed was commented positively upon. In comparison with the ordinary syringe where the plunger rod only protruded approximately 4-5 mm beyond the barrel in a fully depressed state, the plunger rods according to the present invention extend at least 8-9 mm beyond the barrel in a fully depressed state. This allowed the users to obtain a better grip of the plunger rod during filling of the barrel. The distances were measured between the distal end of the barrel and an underside of the head for all three syringes.

Four haemophilia doctors and three haemophilia nurses that were met during this user research also confirmed these statements. None of them preferred the plunger rod of the traditional syringe over any of the two plunger rods according to the present invention.

FIG. 2b shows a cross-section of a detail of a plunger rod 1 of the invention. The uppermost, or distal, part of the head 8 is provided with a coating of for example a thermoplastic elastomer (TPE) (15). This gives a pleasant and soft to the touch feeling for a user. The plunger rod 1 as such is typically made from polypropylene (PP) and injection moulding of plunger rod 1 including the head 8 with its coating of TPE 15 is ideally done more or less in one step. Typically, injection of the TPE would be done from above, i.e. coming from a distal direction towards the plunger rod. However, this has the drawback that the manufacturing takes rather long time since the plunger rod will typically have to be injected in a first step and thereafter the TPE is injected towards the plunger rod and while doing this the air trapped in front of the head of the plunger rod has to evacuate which makes the process time consuming. Also, injecting from above will leave a protruding button which can be perceived as annoying and distract a user or hinder contact with the larger area of the TPE top. According to the present invention, this can be avoided by first injecting the plunger rod 1, for example made from polypropylene, and then immediately afterwards inject the TPE 15 through a channel 14 extending the plunger rod 1. The channel 14 may for example extend between a tip of a leg 7 of the plunger rod 1 and end in the center of head 8. This method improves manufacturing speed of the plunger rod 1 as well as avoiding a protruding button on the top of the TPE-part of head 8.

Figure 3C:
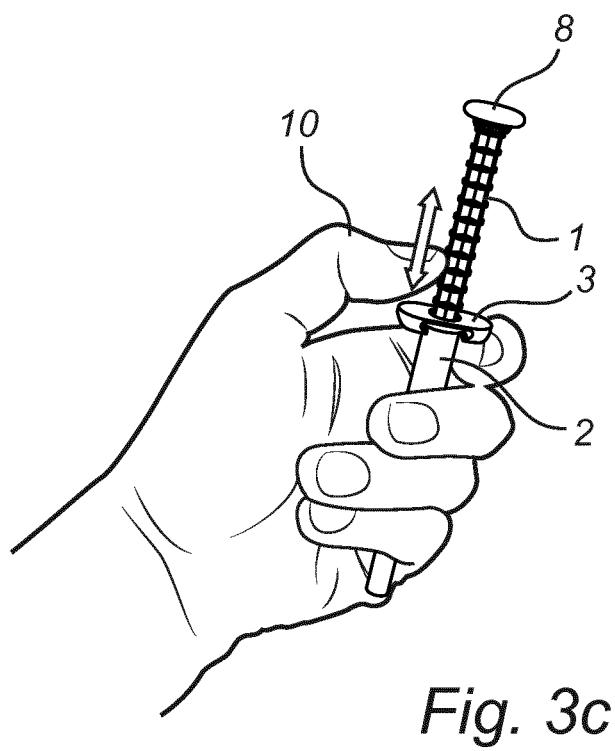
Figure 5:
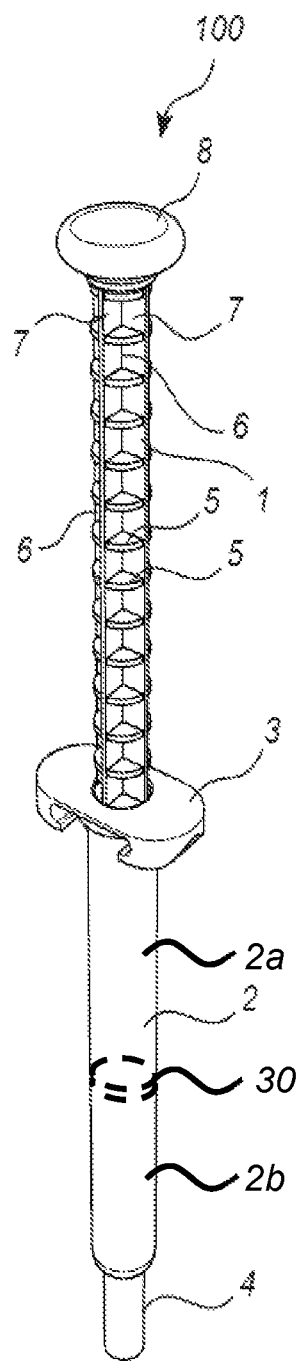
FIG. 5 is a schematic of a barrel of a two-chamber type.

FIGS. 3*a*-3*c* show examples of situations where the plunger rod 1 according to the present invention has particular advantages over the prior art. For example during assembly of the syringe 100, see FIGS. 3*a* and 3*b*, where the plunger rod 1 provides a user with excellent gripping properties in both an axial direction and during rotational movement of the plunger rod 1. The second being applicable when screwing the threaded portion 9 of the plunger rod 1 into the not shown plunger arranged within the barrel 2. FIG. 3*c* shows another situation where the plunger rod 1 according to the present invention is advantageous. A user, using one hand only, and being unable to reach both the upper side and the underside of the head 8 with the thumb 10 can instead place the thumb 10 at any desired location along the plunger rod 1 and manipulate the plunger rod 1 in any direction and with high precision while firmly holding the syringe 100 in the palm of the hand. With prior art syringes, the user would either be forced to use the other hand as well, or if that is impossible, try to somehow reach the head 8 of the plunger rod 1 by excessively stretching out the thumb 10. Even if a user by doing so would be able to reach the underside of the head 8, further retraction of the plunger rod 1, e.g. in order to aspirate, would be impossible or at least very hard, due to the already inconvenient position. At that point, any one-handed injection is more or less excluded since it would probably be extremely difficult to reach the upper side of the head 8. Further, since such stretching out greatly reduces the practicability of keeping the syringe 100 still when inserted into the body, the likelihood of causing micro bleeds or similar is greatly increased. This is of course never desirable but for certain patients, such as persons suffering from haemophilia, it is of an immense importance to avoid any bleedings at all. This problem is effectively avoided with the syringe 100 according to the present invention in that the finger grip enhancing means 5 of the plunger rod 1 allow a user to place a finger, such as a thumb, at any position along the plunger rod 1 such that the syringe 100 can be held comfortably and immovably during aspiration and/or injection. It is even possible to manipulate the plunger rod 1 in steps such that an overstretching of e.g. a thumb is never required. A further gripping position which is enabled by the present invention is when a user positions the thumb against the plunger rod 1, similar to what is shown in FIG. 3*c*, and the index finger against the opposite surface of the plunger rod 1 and then uses both thumb and index finger to manipulate the plunger rod 1.

FIGS. 4*a* and 4*b* show further embodiments of a plunger rod according to the present invention. It should be noted that threaded portion 9 is left out in the side view cross-sections of FIGS. 4*a* and 4*b*. Here, the head 8 of the plunger rod 1 is provided with finger grip enhancing means 11, 12 and 13 in the form of axially protruding ribs. Similar to the above-mentioned grip enhancing means 5, these axially protruding ribs 11, 12 and 13 provide a user with reliable grip during manipulation of the plunger rod 1. These ribs are created during manufacturing of the plunger rod 1 and provide the plunger rod 1 with enhanced grip properties without the requirement of any subsequent coating or similar. In the embodiments shown herein, the head 8 is provided with an outer rib 11, an intermediate rib 12 and an innermost rib 13. Of course other numbers of ribs are conceivable within the scope of the invention. Ribs 11, 12, 13 are shown having an annular shape but of course other shapes are imaginable as well, such as ribs extending in straight lines. The annular shape of the ribs have a major advantage though in that they provide anti-slip properties in all directions of a plane in parallel with the head 8, i.e. perpendicular to the longitudinal axis of the plunger rod 1.

The embodiments shown in FIGS. 4*a* and 4*b* differs from each other in that the first-mentioned has a head 8 having a concave side view cross-section and the other having a convex side view cross-section. Both provide improved anti-slip properties in comparison with a flat head in that the concave cross-section provides a recess in which a finger tip can rest and in that the convex shape will create a kind of protrusion that will be pressed into the finger tip of the user when depressing the plunger rod 1.

It should be noticed that even though the grip enhancing means according to the present invention are presented have hitherto been described as ribs or planar discs extending in a plane generally perpendicular to the longitudinal axis of the plunger rod other formats are conceivable and lie within the scope of the present invention. For example, concave discs could be arranged having a concave surface directed towards the head of the plunger rod. Such discs would provide better grip properties during injection using a finger pressed against to circumferential surface of the plunger rod. This since the concave shape would cause the perimeter of the disc to point up towards the head of the plunger rod. Alternatively, convex discs could be arranged having a convex surface directed towards the head of the plunger rod. Such discs would provide better grip properties during e.g. aspiration using a finger pressed against to circumferential surface of the plunger rod. This since the convex shape would cause the perimeter of the disc to point down, away from the head of the plunger rod. Obviously, different combinations of the three are imaginable as well. For example, concave and convex discs could alternate along the length of the plunger rod or every third disc could be flat.

Further, it would also be possible to provide the perimeter of the ribs or discs with a tapering. The sharp edge thus provided will enhance grip properties further.

In order to further improve user friendliness, it is suggested to provide a plunger rod 1 that has such length that when the plunger rod 1 and plunger is in a most proximal position, i.e. fully depressed, the plunger rod 1 will still protrude somewhat from the barrel 2. This makes it easier for a user to grab the head 8 of the plunger rod 1 during for example filling of the barrel 2 in comparison with syringes where the head of the plunger rod lies adjacent to or even bears against the barrel in the fully depressed position. The plunger rod 1 of this embodiment of the invention could even allow a user who at all times prefers to use a finger, such as a thumb, against the circumferential surface of the plunger rod 1 instead of using the head 8 of the plunger rod 1. This since a certain part of the grip enhancing means 5 of the plunger rod 1 will be accessible also in a fully depressed position of the plunger rod 1.

Finally, it is realized, that a syringe 100 according to the invention has a number of advantages over the known prior art devices. Due to the fact that the syringe 100 has a plunger rod 1 with grip enhancing means 5 provided on an outer surface thereof, a user can manipulate the plunger rod 1 without having to reach for the head 8 of the plunger rod 1. It also ensures safer handling for users with certain needs or requirements, such as children, elderly or persons with impaired moving abilities. It has incomparable qualities for persons with certain diseases such as haemophilia since due to the improved manageability of the syringe, micro bleeds, or worse, can be avoided.

It is to be understood that the embodiments described above and in the drawings are to be regarded only as non-limiting examples of the invention and that they may be modified in many ways within the scope of the claims.

The invention claimed is:

1. A syringe comprising a barrel, a plunger within said barrel arranged to travel within said barrel, and a plunger rod connected to said plunger for driving said plunger in a bidirectional manner, wherein said plunger rod comprises a head at a distal end thereof and wherein said plunger rod further comprises a plurality of protruding circle segment shaped finger grips consecutively axially spaced along a length of the plunger rod, wherein every portion of each circle segment shaped finger grip is axially spaced along said length of said plunger rod from every portion of a consecutive neighboring circle segment shaped finger grip, wherein the circle segment shaped finger grips are provided with a mutual center distance between 3 and 20 mm, wherein said circle segment shaped finger grips are configured such that a patient can place one or more fingers on said circle segment shaped finger grips when the plunger rod is extended in a most distal position, wherein said plunger rod has a cross-shaped cross-section and wherein said circle segment shaped finger grips are arranged in a gap defined by two adjacent legs of the cross-shaped plunger rod, wherein each circle segment shaped finger grip has a length which does not exceed a length of any of said two adjacent legs of the cross-shaped plunger rod, wherein said circle segment shaped finger grips are equally axially spaced along the length of the plunger rod from an underside of a flange of the head to a connecting part of the plunger rod, wherein the plunger rod has a length such that when it has been fully depressed relative to the barrel, the plunger rod extends at least 8 mm from a distal end of the barrel, measured from an underside of the flange of the head.

2. The syringe according to claim 1, wherein said circle segment shaped finger grips comprise a plurality of protruding ribs axially spaced along the length of the plunger rod, wherein said ribs extend generally perpendicularly to a longitudinal axis of the plunger rod.

3. The syringe according to claim 1, wherein said circle segment shaped finger grip are axially spaced along a length of the plunger rod and lying in a plane generally perpendicular to a longitudinal axis of the plunger rod.

4. The syringe according to claim 3, wherein the circle segment shaped finger grips comprise a plurality of elements shaped as circle sectors and wherein arcs of the circle sectors extend between the tips of the two adjacent legs of the plunger rod.

5. The syringe according to claim 3, wherein the circle segment shaped finger grips are arranged in at least two gaps of the plunger rod.

6. The syringe according to claim 1, wherein the circle segment shaped finger grips have a thickness of approximately 0.5-3 mm.

7. The syringe according to claim 1, wherein the circle segment shaped finger grips are provided along substantially the whole length of the part of the plunger rod extending from an underside of the head to a connecting part of the plunger rod.

8. The syringe according to claim 1, wherein the syringe comprises at least three circle segment shaped finger grips.

9. The syringe according to claim 1, wherein the head of the plunger rod is provided with circle segment shaped finger grips.

10. The syringe according to claim 9, wherein the circle segment shaped finger grips of the head of the plunger rod comprise a rib extending in a direction parallel to the longitudinal axis of the plunger rod.

11. The syringe according to claim 9, wherein the circle segment shaped finger grips of the head of the plunger rod comprise a thermoplastic elastomer.

12. The syringe according to claim 1, wherein the head of the plunger rod has a concave shape.

13. The syringe according to claim 1, wherein the head of the plunger rod has a convex shape.

14. The syringe according claim 1, wherein the barrel is of a two-chamber type.

15. The syringe according to claim 1, wherein the circle segment shaped finger grips are sized such that the plunger rod can be driven in a bidirectional manner within said barrel substantially without friction from said barrel.

16. The syringe according to claim 1, wherein the circle segment shaped finger grips are provided with a mutual center distance between 5 and 20 mm.

17. A kit of parts comprising infusion equipment and a medicament to be injected, wherein said infusion equipment comprises a syringe according to claim 1.

18. The kit of parts according to claim 17, wherein the medicament is a medicament for treatment of haemophilia.

* * * * *